United States Patent
Hsieh et al.

(10) Patent No.: US 8,548,118 B2
(45) Date of Patent: Oct. 1, 2013

(54) APPARATUS AND METHOD FOR SPECTRAL PROJECTION IMAGING WITH FAST KV SWITCHING

(75) Inventors: Jiang Hsieh, Brookfield, WI (US); Naveen Chandra, Kenosha, WI (US); Steven J. Woloschek, Franklin, WI (US); Robert F. Senzig, Germantown, WI (US)

(73) Assignee: General Electric Company, Schenectady, NY (US)

( * ) Notice: Subject to any disclaimer, the term of this patent is extended or adjusted under 35 U.S.C. 154(b) by 60 days.

(21) Appl. No.: 12/642,945

(22) Filed: Dec. 21, 2009

(65) Prior Publication Data

US 2011/0150175 A1 Jun. 23, 2011

(51) Int. Cl.
*G01N 23/00* (2006.01)

(52) U.S. Cl.
USPC ....... 378/16; 378/4; 378/5; 378/124; 378/137

(58) Field of Classification Search
USPC .................................. 378/4, 5, 16, 124, 137
See application file for complete search history.

(56) References Cited

U.S. PATENT DOCUMENTS

| | | | |
|---|---|---|---|
| 6,389,097 B1 | 5/2002 | Bulkes et al. | |
| 6,574,304 B1 | 6/2003 | Hsieh et al. | |
| 6,687,329 B1 | 2/2004 | Hsieh et al. | |
| 7,187,756 B2 * | 3/2007 | Gohno et al. | 378/124 |
| 7,310,436 B2 | 12/2007 | Li et al. | |
| 7,457,451 B2 | 11/2008 | Hsieh et al. | |
| 2003/0195416 A1* | 10/2003 | Toth | 600/427 |
| 2004/0101087 A1* | 5/2004 | Hsieh et al. | 378/4 |
| 2005/0084073 A1* | 4/2005 | Seppi et al. | 378/156 |
| 2005/0220265 A1* | 10/2005 | Besson | 378/16 |
| 2007/0003020 A1* | 1/2007 | Hsieh et al. | 378/207 |
| 2008/0080662 A1* | 4/2008 | Shukla | 378/4 |
| 2008/0212853 A1* | 9/2008 | Lin et al. | 382/128 |
| 2008/0247504 A1* | 10/2008 | Edic et al. | 378/9 |
| 2009/0161816 A1* | 6/2009 | De Man et al. | 378/9 |
| 2010/0067651 A1* | 3/2010 | Hsieh et al. | 378/17 |

* cited by examiner

*Primary Examiner* — Toan Ton
*Assistant Examiner* — Mona M Sanei
(74) *Attorney, Agent, or Firm* — Ziolkowski Patent Solutions Group, SC

(57) ABSTRACT

A CT system includes a gantry, an x-ray source configured to project x-rays toward an object, an x-ray detector positioned to receive x-rays from the x-ray source that pass through the object, a generator configured to energize the x-ray source to a first voltage and to a second voltage that is distinct from the first voltage, and a controller configured to cause the gantry to position the source and generator at a circumferential position during an imaging session, pass the object through the opening during the imaging session, cause the generator to energize the x-ray source to the first voltage and to the second voltage, acquire imaging data while the generator energizes the x-ray source to the first voltage and to the second voltage while the rotatable gantry is at the circumferential position, and generate an image using the imaging data.

22 Claims, 5 Drawing Sheets

APPARATUS AND METHOD FOR SPECTRAL PROJECTION IMAGING WITH FAST KV SWITCHING

BACKGROUND OF THE INVENTION

Embodiments of the invention relate generally to diagnostic imaging and, more particularly, to an apparatus and method of spectral projection imaging (SPI) with fast kV switching.

Typically, in computed tomography (CT) imaging systems, an x-ray source emits a fan-shaped beam toward a subject or object, such as a patient or a piece of luggage. Hereinafter, the terms "subject" and "object" shall include anything capable of being imaged. The beam, after being attenuated by the subject, impinges upon an array of radiation detectors. The intensity of the attenuated beam radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis which ultimately produces an image.

Generally, the x-ray source and the detector array are rotated about the gantry within an imaging plane and around the subject. X-ray sources typically include x-ray tubes, which emit the x-ray beam at a focal point. X-ray detectors typically include a collimator for collimating x-ray beams received at the detector, a scintillator for converting x-rays to light energy adjacent the collimator, and photodiodes for receiving the light energy from the adjacent scintillator and producing electrical signals therefrom. Typically, each scintillator of a scintillator array converts x-rays to light energy. Each scintillator discharges light energy to a photodiode adjacent thereto. Each photodiode detects the light energy and generates a corresponding electrical signal. The outputs of the photodiodes are then transmitted to the data processing system for image reconstruction.

A CT imaging system may include an energy discriminating (ED), multi energy (ME), and/or dual-energy (DE) CT imaging system that may be referred to as an EDCT, MECT, and/or DE-CT imaging system. Such systems may use a scintillator or a direct conversion detector material in lieu of the scintillator. The EDCT, MECT, and/or DE-CT imaging system in an example is configured to be responsive to different x-ray spectra. For example, a conventional third generation CT system may acquire projections sequentially at different peak kilovoltage (kVp) levels, which changes the peak and spectrum of energy of the incident photons comprising the emitted x-ray beams. Energy sensitive detectors may be used such that each x-ray photon reaching the detector is recorded with its photon energy.

Techniques to obtain the measurements comprise: (1) scan with two distinctive energy spectra; and (2) detect photon energy according to energy deposition in the detector. EDCT/MECT/DE-CT provides energy discrimination and material characterization. For example, in the absence of object scatter, the system derives the behavior at a different energy based on the signal from two regions of photon energy in the spectrum: the low-energy and the high-energy portions of the incident x-ray spectrum. In a given energy region of medical CT, two physical processes dominate the x-ray attenuation: (1) Compton scatter and the (2) photoelectric effect. The detected signals from two energy regions provide sufficient information to resolve the energy dependence of the material being imaged. Furthermore, detected signals from the two energy regions provide sufficient information to determine the relative composition of an object composed of two hypothetical materials.

A principle objective of dual-energy scanning is to obtain diagnostic CT images that enhance contrast separation within the image by utilizing two scans at different chromatic energy states. A number of techniques have been proposed to achieve dual-energy scanning including acquiring two scans either (1) back-to-back sequentially in time where the scans require two rotations around the subject, or (2) interleaved as a function of the rotation angle requiring one rotation around the subject, in which the tube operates at, for instance, 80 kVp and 140 kVp potentials. High frequency generators have made it possible to switch the kVp potential of the high frequency electromagnetic energy projection source on alternating views. As a result, data for two images at different energies may be obtained in a temporally interleaved fashion rather than two separate scans made several seconds apart as required with previous CT technology.

Using the images obtained during these CT scans, one can generate basis material density images and monochromatic images, that is, images that represent the effect of performing a computed tomography scan with an ideal monochromatic tube source. Given a pair of material density images, it is possible to generate other basis material image pairs. For example, from a water and iodine image of the same anatomy, it is possible to generate a different pair of material density images such as calcium and gadolinium. Or, by using a pair of basis material images, one can generate a pair of monochromatic images, each at a specific x-ray energy. Similarly, one can obtain, from a pair of monochromatic images, a pair of basis material image pairs, or a pair of monochromatic images at different energies.

CT scanning, either conventional CT scanning at one polychromatic energy or at dual-energy, can result in excess dose to a patient. For instance, when scanning an object such as a patient, typically a scout scan is performed where the patient is passed through an imaging system while components of the imaging system remain stationary. The goal of a scout scan is typically to identify locations or regions of interest for performing a full CT scan. A scout scan is typically performed with low mA and provides projection views along a single axis along the patient being imaged, and typically provides projections that each includes an aggregation of the internal structures of the patient. Further, scout data in CT does not contain adequate information for three-dimensional (3D) image reconstruction, because data is typically obtained along the single axis of the object being imaged and at a particular projection angle. And, at times it may be difficult to identify specific fine structure of the patient based on a scout scan due to the overlapping structures. Nevertheless, a scout scan may be used to identify internal structure and organs of the patient in order to establish a region-of-interest (ROI) of a patient for performing a full CT scan and target imaging of a suspected pathology.

However, because scout images aggregate internal structures therein and cannot typically be used to reconstruct a 3D image, it can be difficult to interpret a scout scan, and internal structures therein can be masked and difficult to see. Thus, an imaging session based on a scout scan may be planned that misses a suspected pathology altogether. Or, because of unclarity in the scout image, it is sometimes necessary to scan additional lengths or regions of an object to ensure that a suspected pathology is captured in the imaging region or the identified ROI. Thus, despite taking a scout scan, it may be necessary at times to re-scan a patient or unnecessarily scan additional regions of an object in order to properly identify and diagnose a pathology, leading to additional x-ray dose to the patient.

Known scanning techniques include dual-energy scanning in an x-ray radiography system having, typically, a digital flat panel therein. However, such techniques are typically performed with a low/high kVp switching speed that is greater than 125 ms, which can lead to mis-registration artifacts and a loss of image resolution. Further, although images obtained therefrom may be helpful in determining a location of a pathology in a patient, in order to scan the region with 3D imaging techniques, it is typically necessary to transfer the object or patient to another imaging system or modality in order to generate and obtain the 3D imaging data. Thus, not only can dual-energy x-ray radiography imaging result in images that may include mis-registration and other imaging artifacts, it also includes inconvenience and additional cost to move the object or patient to a 3D imaging system and use images obtained from the dual-energy x-ray scan for obtaining 3D information.

Therefore, it would be desirable to design a system and method for improving scout scan data in an imaging system.

BRIEF DESCRIPTION OF THE INVENTION

Embodiments of the invention are directed toward a system and method and apparatus for acquiring dual-energy imaging data.

According to an aspect of the present invention, a CT system includes a rotatable gantry having an opening for receiving an object to be scanned, an x-ray source positioned on the rotatable gantry and configured to project x-rays toward the object, an x-ray detector positioned on the rotatable gantry and positioned to receive x-rays from the x-ray source that pass through the object, a generator configured to energize the x-ray source to a first voltage and configured to energize the x-ray source to a second voltage, the first voltage distinct from the second voltage, and a controller configured to cause the rotatable gantry to position the x-ray source and the x-ray generator at a circumferential position during an imaging session, pass the object through the opening during the imaging session, cause the generator to energize the x-ray source to the first voltage and to the second voltage during the imaging session, acquire imaging data while the generator energizes the x-ray source to the first voltage, while the generator energizes the x-ray source to the second voltage, and while the rotatable gantry is at the circumferential position, and generate an image using the imaging data.

According to another aspect of the present invention, a method of CT imaging includes passing an object through an opening of a CT system a first time, projecting a first beam of x-ray energy through the object while a gantry of the CT system remains stationary, the first beam of x-ray energy generated at a first voltage, acquiring a first projection from the first beam of x-ray energy that projects through the object, projecting a second beam of x-ray energy through the object while the gantry of the CT system remains stationary, the second beam of x-ray energy generated at a second voltage, acquiring a second projection from the second beam of x-ray energy that projects through the object, and reconstructing an image using the first projection and the second projection.

According to yet another aspect of the present invention, a controller is configured to acquire imaging data at more than one chromatic energy state, wherein the controller is further configured to cause an object to pass through an opening of a gantry while causing the gantry to remain stationary, cause an x-ray source to be energized to a first voltage potential and to project a first x-ray beam toward the object, cause acquisition of a first set of data from the first x-ray beam, cause the x-ray source to be energized to a second voltage potential and to project a second x-ray beam toward the object, cause acquisition of a second set of data from the second x-ray beam, and reconstruct an image using the first set of data and the second set of data.

Various other features and advantages of the present invention will be made apparent from the following detailed description and the drawings.

BRIEF DESCRIPTION OF THE DRAWINGS

The drawings illustrate one preferred embodiment presently contemplated for carrying out the invention.

In the drawings.

DETAILED DESCRIPTION

Diagnostics devices comprise x-ray systems, magnetic resonance (MR) systems, ultrasound systems, computed tomography (CT) systems, positron emission tomography (PET) systems, ultrasound, nuclear medicine, and other types of imaging systems. Applications of x-ray sources comprise imaging, medical, security, and industrial inspection applications. However, it will be appreciated by those skilled in the art that an implementation is applicable for use with single-slice or other multi-slice configurations. Moreover, an implementation is employable for the detection and conversion of x-rays. However, one skilled in the art will further appreciate that an implementation is employable for the detection and conversion of other high frequency electromagnetic energy. An implementation is employable with a "third generation" CT scanner and/or other CT systems.

The operating environment of the present invention is described with respect to a sixty-four-slice computed tomography (CT) system. However, it will be appreciated by those skilled in the art that the present invention is equally applicable for use with other multi-slice configurations.

Figure 1:
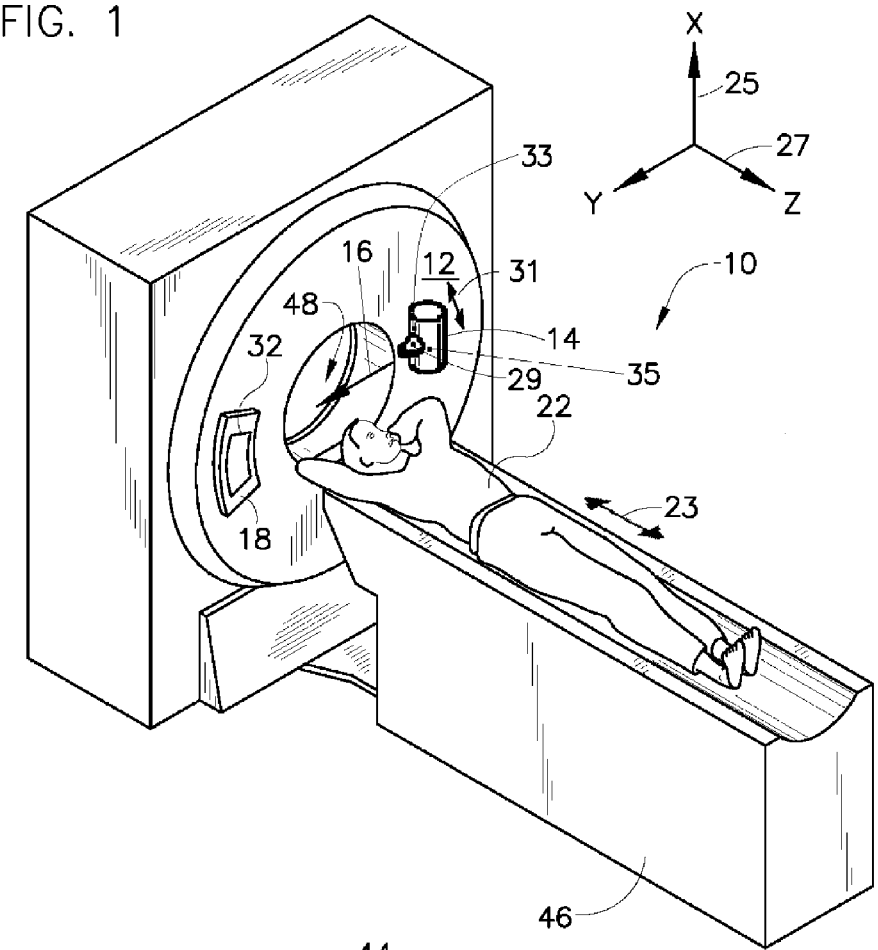
FIG. 1 is a pictorial view of a CT imaging system.
Figure 2:
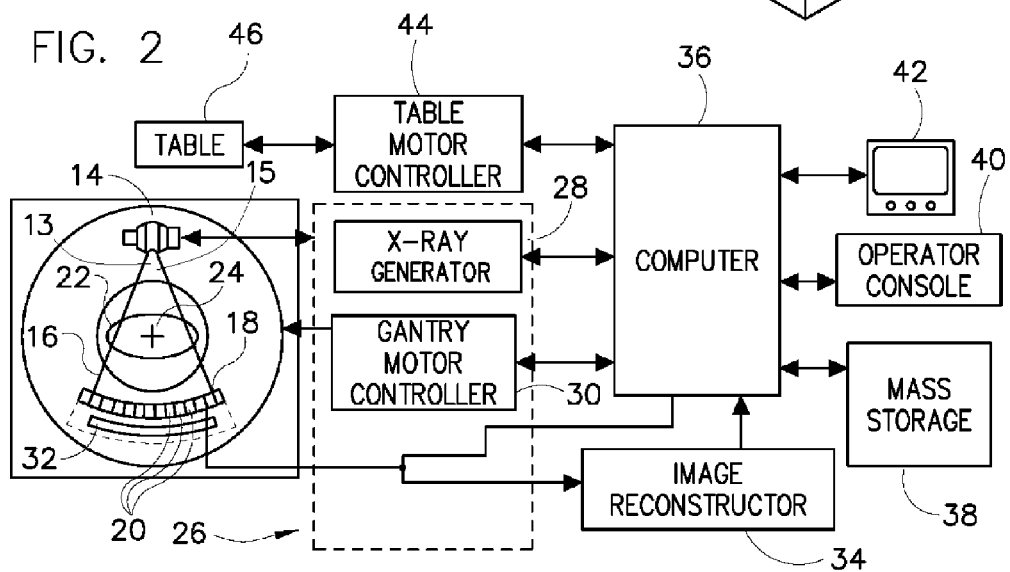
FIG. 2 is a block schematic diagram of the system illustrated in FIG. 1.

Referring to FIG. 1, a computed tomography (CT) imaging system 10 is shown as including a gantry 12 representative of a "third generation" CT scanner. Gantry 12 has an x-ray source 14 that projects a polychromatic beam of x-rays 16 toward a detector assembly or collimator 18 on the opposite side of the gantry 12. Referring now to FIG. 2, detector assembly 18 is formed by a plurality of detectors 20 and data acquisition systems (DAS) 32. The plurality of detectors 20 sense the projected x-rays that pass through a medical patient 22 that is traveling in a direction of object travel 23, and DAS 32 converts the data to digital signals for subsequent processing. Each detector 20 produces an analog electrical signal that represents the intensity of an impinging x-ray beam and hence the attenuated beam as it passes through the patient 22. During a scan to acquire x-ray projection data, gantry 12 and the components mounted thereon rotate about a center of rotation 24. CT imaging system 10 is a dual-energy system, in that energy is projected from x-ray source 14 at different chromatic energy states in order to enhance contrast separation within the image.

Rotation of gantry 12 and the operation of x-ray source 14 are governed by a control mechanism 26 of CT system 10. Control mechanism 26 includes an x-ray generator 28 that provides power and timing signals to an x-ray source 14 and a gantry motor controller 30 that controls the rotational speed and position of gantry 12. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has some form of operator interface, such as a keyboard, mouse, voice activated controller, or any other suitable input apparatus. An associated display 42 allows the operator to observe the reconstructed image and other data from computer 36. The operator supplied commands and parameters are used by computer 36 to provide control signals and information to DAS 32, x-ray generator 28 and gantry motor controller 30. In addition, computer 36 operates a table motor controller 44 which controls a motorized table 46 to position patient 22 and gantry 12. Particularly, table 46 moves patients 22 through a gantry opening 48 of FIG. 1 in whole or in part.

Figure 3:
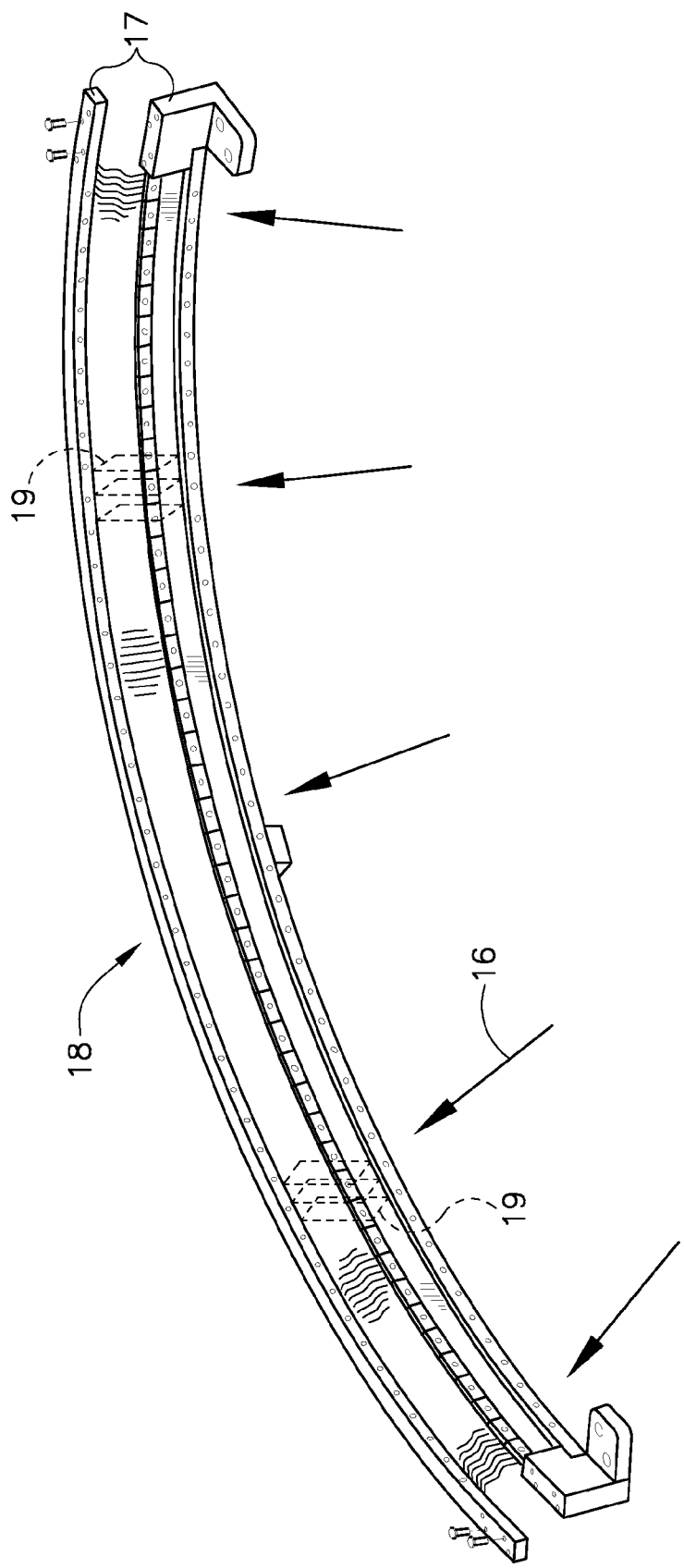
FIG. 3 is a perspective view of one embodiment of a CT system detector array.

As shown in FIG. 3, detector assembly 18 includes rails 17 having collimating blades or plates 19 placed therebetween. Plates 19 are positioned to collimate x-rays 16 before such beams impinge upon, for instance, detector 20 of FIG. 4 positioned on detector assembly 18. In one embodiment, detector assembly 18 includes 57 detectors 20, each detector 20 having an array size of 64×16 of pixel elements 50. As a result, detector assembly 18 has 64 rows and 912 channels (16×57 detectors) which allows 64 simultaneous slices of data to be collected with each rotation of gantry 12.

Figure 4:
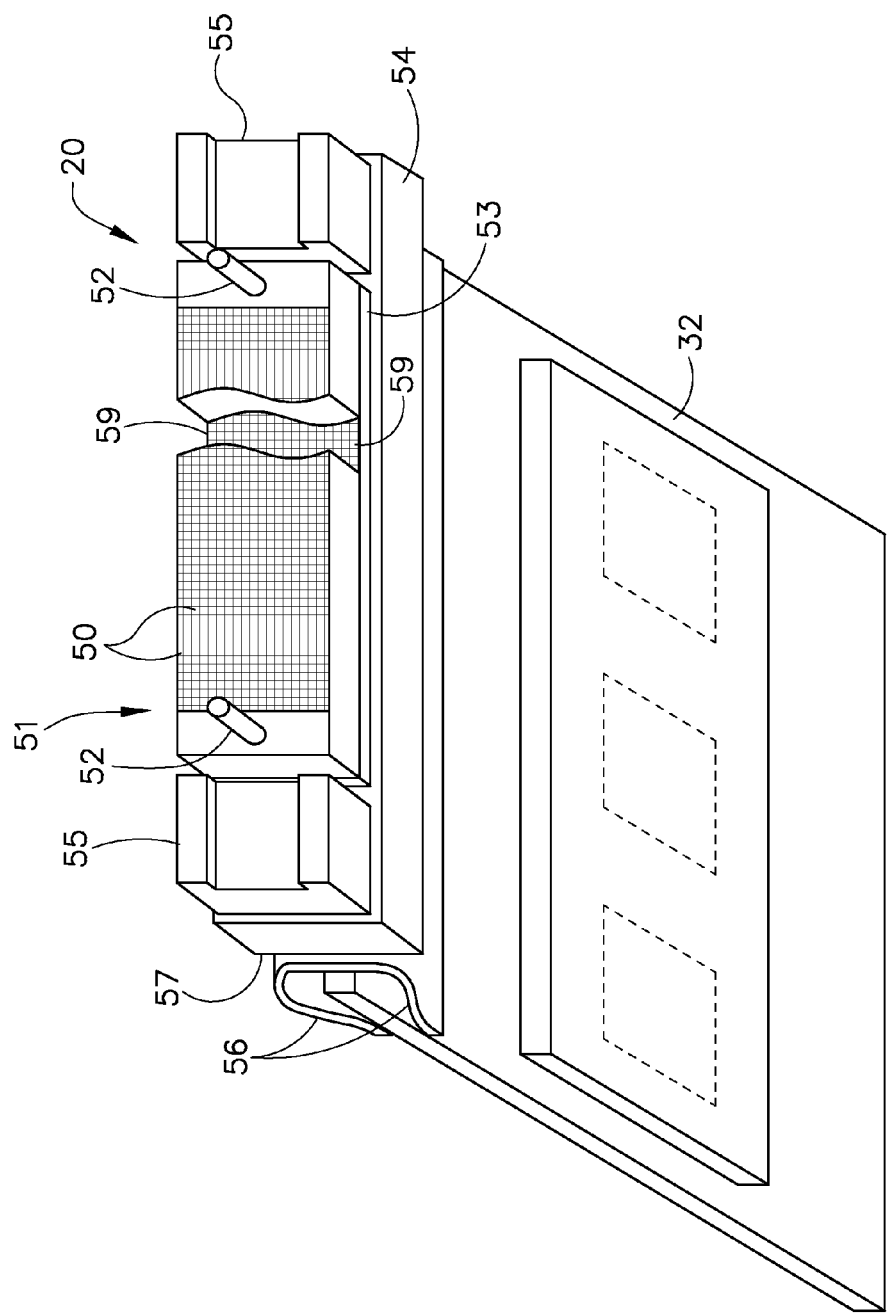
FIG. 4 is a perspective view of one embodiment of a detector.

Referring to FIG. 4, detector 20 includes DAS 32, with each detector 20 including a number of detector elements 50 arranged in pack 51. Detectors 20 include pins 52 positioned within pack 51 relative to detector elements 50. Pack 51 is positioned on a backlit diode array 53 having a plurality of diodes 59. Backlit diode array 53 is in turn positioned on multi-layer substrate 54. Spacers 55 are positioned on multi-layer substrate 54. Detector elements 50 are optically coupled to backlit diode array 53, and backlit diode array 53 is in turn electrically coupled to multi-layer substrate 54. Flex circuits 56 are attached to face 57 of multi-layer substrate 54 and to DAS 32. Detectors 20 are positioned within detector assembly 18 by use of pins 52.

In the operation of one embodiment, x-rays impinging within detector elements 50 generate photons which traverse pack 51, thereby generating an analog signal which is detected on a diode within backlit diode array 53. The analog signal generated is carried through multi-layer substrate 54, through flex circuits 56, to DAS 32 wherein the analog signal is converted to a digital signal.

Figure 5:
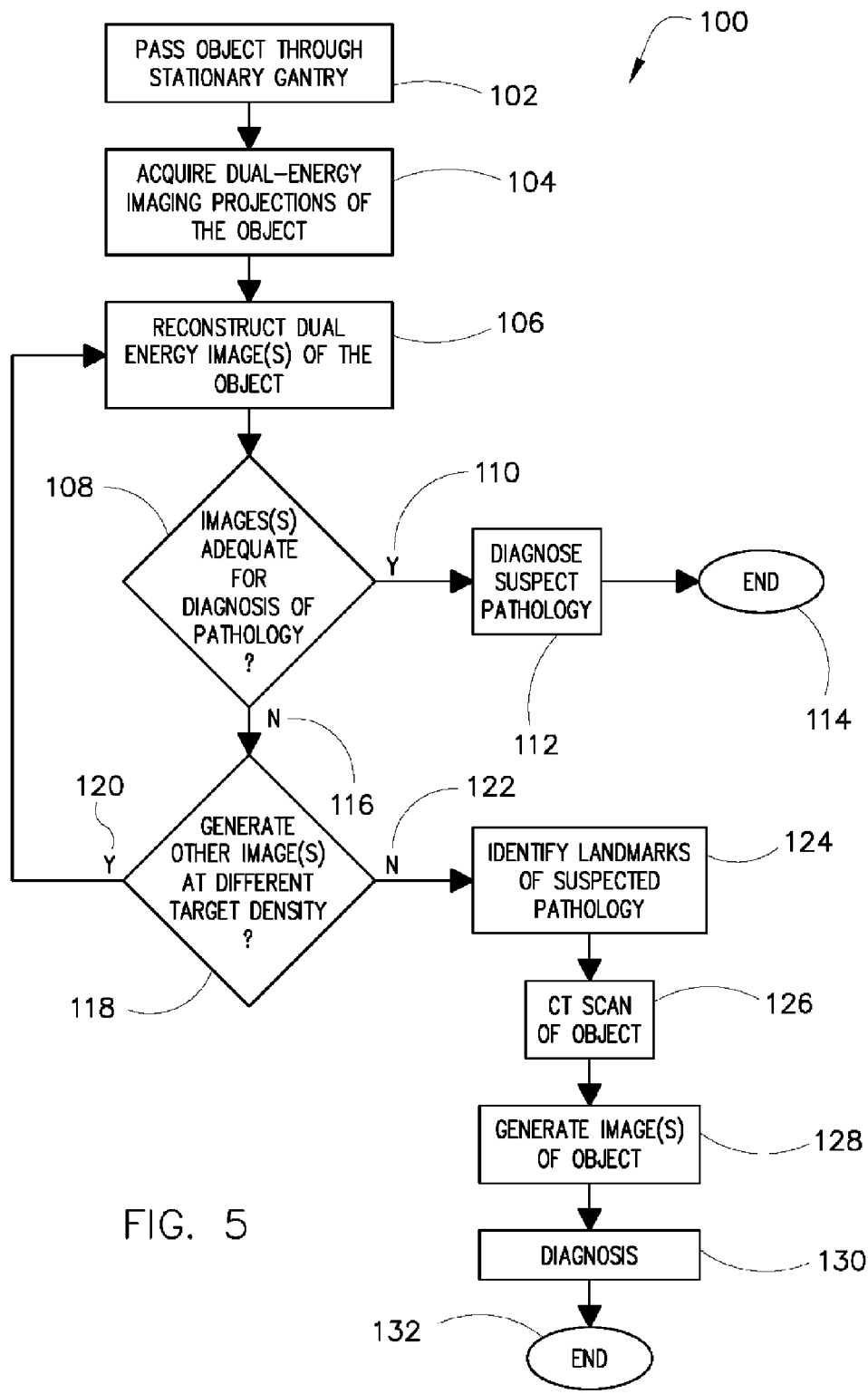
FIG. 5 is a spectral projection imaging (SPI) technique for scanning an object according to an embodiment of the invention.

Referring to FIG. 5, a spectral projection imaging (SPI) technique 100 is illustrated according to an embodiment of the invention. Technique 100 includes passing an object through a stationary gantry such as gantry 12 in the direction of object travel 23, of CT imaging system 10, as illustrated at step 102. During the imaging process, the patient is translated perpendicular to the x-ray imaging plane. The translation can be continuous motion or discrete motion, can be at a constant speed, or at a variable speed. At step 104, dual-energy projection data is acquired of the object while the gantry remains stationary and while the object moves through the gantry, by causing a generator, such as generator 28 of CT system 10 as described above, to output a first voltage and a second voltage to an x-ray tube in a fast-switching pattern to cause x-rays 16, illustrated in FIG. 2, to emit as a first beam 13 and a second beam 15, to emit therefrom having x-rays energies corresponding respectively to the first voltage and the second voltage. In one embodiment, the generator causes the first voltage and the second voltage to be switched at a 2 kHz frequency, and in other embodiments, the generator causes the first voltage and the second voltage to be switched at frequencies of 550 Hz and greater. By rapidly switching the x-ray tube voltage with a synchronized DAS sampling at a stable speed of, for instance, 100 mm/s, overlapped projection samples may be obtained for both low and high kVp settings. However, the invention is not to be so limited and according to one embodiment of the invention the table speed may vary between 100-175 mm/sec, and according to other embodiments the table speed may be from 0-200 mm/sec or greater. In embodiments of the invention, the second voltage is greater than the first voltage. In one embodiment the first voltage is 80 kVp and the second voltage is 140 kVp, and in another embodiment the first voltage is 100 kVp and the second voltage is 120 kVp. One skilled in the art will recognize that any combination of voltages may be used for the respective first and second voltages in order to generate dual-energy data. According to embodiments of the invention, technique 100 includes obtaining dual-energy projection data at step 104 having mA's that are lower than in conventional dual-energy imaging. In other embodiments, the dual-energy data obtained is at mA between 20-200. In another embodiment, a pre-patient collimator can be used to collimate the x-ray beam (in the z direction) to a narrow beam width to reduce the x-ray dose to the patient. In yet another embodiment, the pre-patient collimation can be dynamically adjusted during the data acquisition to equalize the noise in the final reconstructed image based on the patient anatomy variation. In yet another embodiment, the x-ray voltage can be changed continuously (instead of discrete dual energy levels of 80 kVp and 140 kVp) during the data acquisition to produce multiple energy levels and to equalize the flux received by the detector.

These projection samples then undergo multiple calibration steps similar to that of a CT projection to remove detector gain variation, x-ray tube fluctuation, beam-hardening effects, and other non-ideal conditions, as examples. The calibrated projection samples, $p_L(\gamma, \beta, n)$ and $p_H(\gamma, \beta, n)$, are further processed to produce material-density projections, $p_A(\gamma, \beta, n)$ and $p_B(\gamma, \beta, n)$:

$$p_A(\gamma, \beta, n) = \sum_k w_{AL,k} p_L^k(\gamma, \beta, n) + \sum_k w_{AH,k} p_H^k(\gamma, \beta, n) + \sum_{k,j} w_{ALH,kj} p_L^k(\gamma, \beta, n) p_H^j(\gamma, \beta, n)$$

$$p_B(\gamma, \beta, n) = \sum_k w_{BL,k} p_L^k(\gamma, \beta, n) + \sum_k w_{BH,k} p_H^k(\gamma, \beta, n) + \sum_{k,j} w_{BL,kj} p_L^k(\gamma, \beta, n) p_H^j(\gamma, \beta, n)$$

where $p_L$ and $p_H$ correspond to low and high kVp projections, respectively. $\gamma$ refers to a fan angle, $\beta$ refers to a view angle, and n refers to a detector row width of a CT system, such as system 10 of FIG. 1.

In yet another embodiment, a focal spot 29 of the x-ray tube is caused to deflect in an X direction 25, that is orthogonal to the direction of object travel 23, or a Z direction 27 with respect to the x-ray tube in order to improve resolution of images derived therefrom. In other words, the focal spot 29 may be caused to deflect in a circumferential direction 31 of a CT gantry (such as gantry 12 of FIG. 1) that is substantially orthogonal to x-rays 16 passing through object 22, to a second focal spot location 33. Or, the focal spot may be caused to deflect in a slice direction 27 of a CT gantry that is also substantially orthogonal to x-rays passing through object 22, to a third focal spot location 35. In another embodiment, the focal spot 29 may be caused to deflect in both X 25 and Z 27 directions during acquisition of data. As understood in the art, such deflection may be controlled by a controller such as the controller 30 of FIGS. 1 and 2. Further, switching and/or deflection in X or Z may be synchronized with the passage of object 22 passing through gantry 12.

At step 106, one or more dual-energy images of the object is generated or reconstructed using the dual-energy data. As understood in the art, such data may be used to generate two-dimensional (2D) base material density images that may be manipulated or processed to generate images of a specific density that may help in identification, characterization, and diagnosis of a medical condition, pathology, or materials in an image. For instance, such images may include bone-density, soft-tissue, calcium, water, iodine, or fat content, as examples. Thus, dual-energy projections obtained may be manipulated or processed in order to generate images that can be targeted toward a specific density or material that may be known or related to a suspected pathology. Images may be generated that highlight a target material or density that may be used to A) better locate a suspected pathology as compared to a conventional/single-energy scout scan, or B) diagnose a pathology. Because of the rapid sampling between two kVps in SPI, SPI substantially reduces potential mis-registration artifacts. Thus, although the use of a scout as localizer is well recognized in CT, SPI can be used not only to provide improved guidance to the dual-energy CT acquisition and analysis, but also to provide diagnostic information.

As such, at step 108, image(s) generated at step 106 are assessed, and it is determined whether the image(s) are adequate to diagnose a suspect pathology therewith. If so 110, then a suspected pathology is diagnosed at step 112 using the one or more dual-energy images of the object, after which technique 100 ends at step 114. If the images are not adequate 116, then technique 100 includes assessing whether to generate additional images with different target densities or different materials at step 118 using the imaging data acquired at step 104. If additional images are to be generated 120, then control returns to step 106, and dual-energy image(s) are again generated based on the dual-energy imaging data or projections obtained at step 104 but with different target densities and/or different materials. The iterative step passing from step 118 and back to step 106 essentially allows images to be re-generated or adjusted based on the dual-energy imaging projections acquired at step 104. As such, images may be adjusted or re-generated in order to better identify a suspected pathology based on the needs of the user and/or based on predetermined automated anatomically targeted protocols. As understood in the art, once decomposition of dual-energy data is done, then other images or image pairs having different densities may be generated therefrom. In addition, synthesized monochromatic energy images can be generated based on the basis material pair density images using weighted summation.

However, if additional images are not to be generated 122, then the images generated at step 106 may be used to identify landmarks or a location of a suspected pathology at step 124. Once landmarks are identified, then the object is scanned at step 126. In one embodiment the scan at step 126 is a dual-energy CT scan, with low and high energies at, respectively, 80 kVp and 140 kVp, as examples. In another embodiment of the invention, the scan conducted at step 126 is a CT scan at a single polychromatic energy. One or more CT images are generated at step 128 using the data acquired at step 126, and diagnosis is performed at step 130, after which technique 100 ends at step 132.

Accordingly, technique 100 allows dose efficient segmentation of CT examinations that include dual-energy and mixed exam types. Technique 100 not only includes an improved capability for landmark identification and definition, but includes an ability to forego a helical or axial CT scan altogether. In the case of landmark identification, because landmarks and possible pathologies in an object may be better recognized or identified in the SPI technique described, it is possible to better pinpoint an area or region-of-interest for a full scan, and overall dose is thereby reduced. In the case of foregoing a helical or axial CT scan altogether, because SPI enables dual-energy images to be generated, diagnosis capability is improved when compared to a conventional scout scan. For instance, images that include bone-density, soft-tissue, calcium, water, iodine, or fat content, as examples, may be generated and evaluated—yielding an improved diagnostic capability when compared to a conventional scout scan. As such, dose from a full helical or axial CT scan may be foregone altogether, thus reducing dose to a patient.

Figure 6:
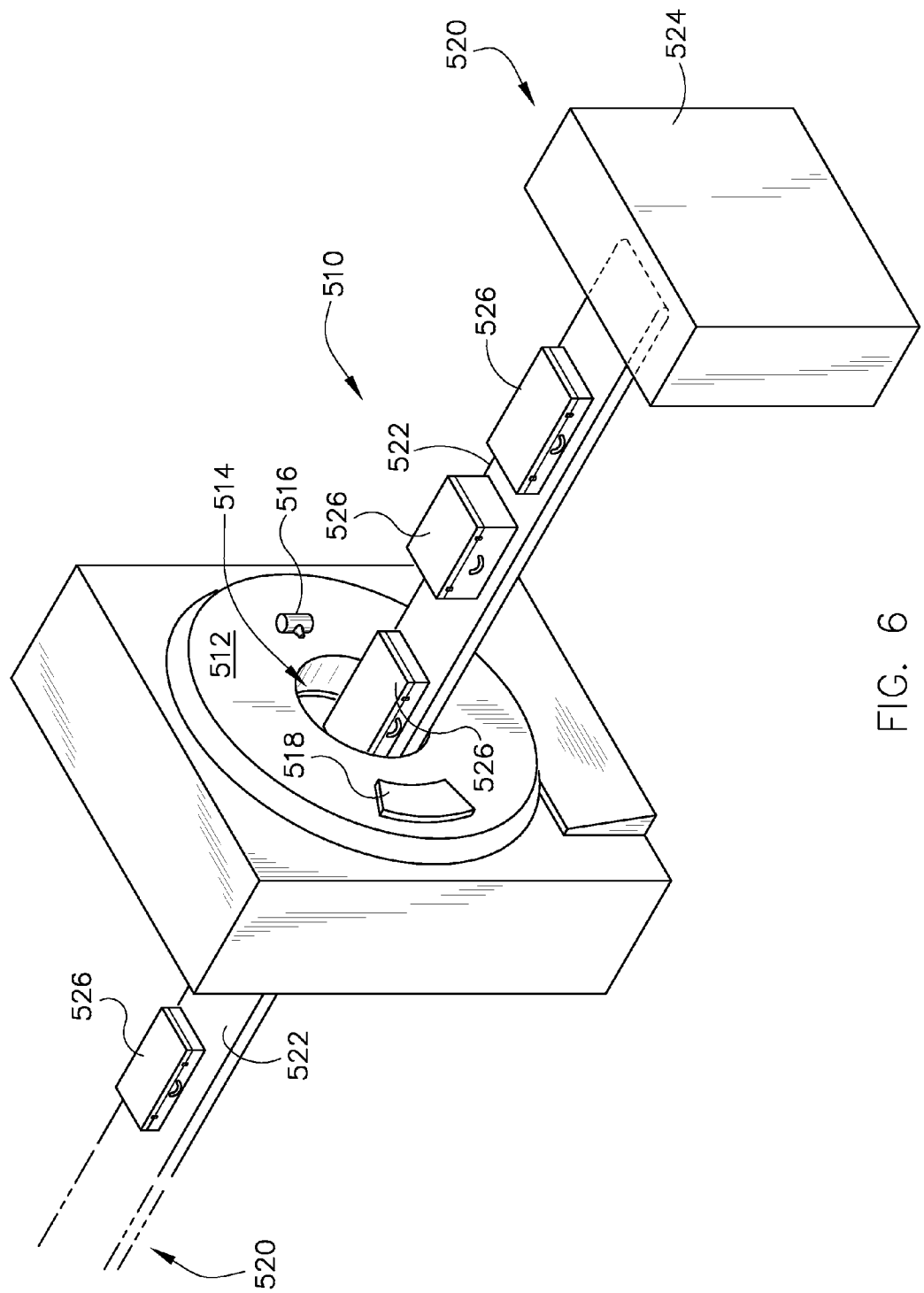
FIG. 6 is a pictorial view of a CT system for use with a non-invasive package inspection system according to an embodiment of the present invention.

FIG. 6 is a pictorial view of an x-ray system 510 for use with a non-invasive package inspection system. The x-ray system 510 includes a gantry 512 having an opening 514 therein through which packages or pieces of baggage may pass. The gantry 512 houses a high frequency electromagnetic energy source, such as an x-ray tube 516, and a detector assembly 518. A conveyor system 520 is also provided and includes a conveyor belt 522 supported by structure 524 to automatically and continuously pass packages or baggage pieces 526 through opening 514 to be scanned. Objects 526 are fed through opening 514 by conveyor belt 522, imaging data is then acquired, and the conveyor belt 522 removes the packages 526 from opening 514 in a controlled and continuous manner. As a result, postal inspectors, baggage handlers, and other security personnel may non-invasively inspect the contents of packages 526 for explosives, knives, guns, contraband, etc. One skilled in the art will recognize that gantry 512 may be stationary or rotatable. In the case of a rotatable gantry 512, system 510 may be configured to operate as a CT system for baggage scanning or other industrial or medical applications.

An implementation of embodiments of the invention in an example comprises a plurality of components such as one or more of electronic components, hardware components, and/or computer software components. A number of such components can be combined or divided in an implementation of the embodiments of the invention. An exemplary component of an implementation of the embodiments of the invention employs and/or comprises a set and/or series of computer instructions written in or implemented with any of a number of programming languages, as will be appreciated by those skilled in the art.

An implementation of the embodiments of the invention in an example employs one or more computer readable storage media. An example of a computer-readable storage medium for an implementation of embodiments of the invention comprises the recordable data storage medium of the image reconstructor 34, and/or the mass storage device 38 of the computer 36. A computer-readable storage medium for an implementation of embodiments of the invention in an example comprises one or more of a magnetic, electrical, optical, biological, and/or atomic data storage medium. For example, an implementation of the computer-readable signal-bearing medium comprises floppy disks, magnetic tapes, CD-ROMs, DVD-ROMs, hard disk drives, and/or electronic memory.

A technical contribution for the disclosed method and apparatus is that it provides for a computer implemented method of spectral projection imaging (SPI) with fast kV switching.

Therefore, according to an embodiment of the present invention, a CT system includes a rotatable gantry having an opening for receiving an object to be scanned, an x-ray source positioned on the rotatable gantry and configured to project x-rays toward the object, an x-ray detector positioned on the rotatable gantry and positioned to receive x-rays from the x-ray source that pass through the object, a generator configured to energize the x-ray source to a first voltage and configured to energize the x-ray source to a second voltage, the first voltage distinct from the second voltage, and a controller configured to cause the rotatable gantry to position the x-ray source and the x-ray generator at a circumferential position during an imaging session, pass the object through the opening during the imaging session, cause the generator to energize the x-ray source to the first voltage and to the second voltage during the imaging session, acquire imaging data while the generator energizes the x-ray source to the first voltage, while the generator energizes the x-ray source to the second voltage, and while the rotatable gantry is at the circumferential position, and generate an image using the imaging data.

According to another embodiment of the present invention, a method of CT imaging includes passing an object through an opening of a CT system a first time, projecting a first beam of x-ray energy through the object while a gantry of the CT system remains stationary, the first beam of x-ray energy generated at a first voltage, acquiring a first projection from the first beam of x-ray energy that projects through the object, projecting a second beam of x-ray energy through the object while the gantry of the CT system remains stationary, the second beam of x-ray energy generated at a second voltage, acquiring a second projection from the second beam of x-ray energy that projects through the object, and reconstructing an image using the first projection and the second projection.

According to yet another embodiment of the present invention, a controller is configured to acquire imaging data at more than one chromatic energy state, wherein the controller is further configured to cause an object to pass through an opening of a gantry while causing the gantry to remain stationary, cause an x-ray source to be energized to a first voltage potential and to project a first x-ray beam toward the object, cause acquisition of a first set of data from the first x-ray beam, cause the x-ray source to be energized to a second voltage potential and to project a second x-ray beam toward the object, cause acquisition of a second set of data from the second x-ray beam, and reconstruct an image using the first set of data and the second set of data.

The present invention has been described in terms of the preferred embodiment, and it is recognized that equivalents, alternatives, and modifications, aside from those expressly stated, are possible and within the scope of the appending claims.

What is claimed is:

1. A CT system comprising:
a rotatable gantry having an opening for receiving an object to be scanned;
an x-ray source positioned on the rotatable gantry and configured to project x-rays toward the object;
an x-ray detector positioned on the rotatable gantry and positioned to receive x-rays from the x-ray source that pass through the object;
a generator configured to energize the x-ray source to a first voltage and configured to energize the x-ray source to a second voltage, the first voltage distinct from the second voltage; and
a controller configured to:
cause the rotatable gantry to be stationary and to position the x-ray source and the x-ray detector at a circumferential position during an imaging session;
pass the object through the opening during the imaging session;
cause the generator to energize the x-ray source to the first voltage and the second voltage during the imaging session;
acquire CT scout imaging data:
while the generator energizes the x-ray source to the first voltage and while the rotatable gantry remains stationary at the circumferential position; and
while the generator energizes the x-ray source to the second voltage and while the rotatable gantry remains stationary at the circumferential position; and
generate a dual-energy scout image using the CT scout imaging data; and
determine additional CT tomographic data acquisition based on the dual-energy scout image, wherein, in determining additional CT tomographic data acquisition based on the dual-energy scout image, the controller is further configured to:
determine if the image is adequate to diagnose a suspect pathology therewith; and
determine whether to generate additional images if the image is not adequate to diagnose the suspect pathology, with any additional images that are generated being generated using the imaging data but with different target densities or different materials, so as provide for diagnosing of the suspect pathology.

2. The CT system of claim 1 wherein the controller is configured to cause the generator to energize the x-ray source to the first voltage and subsequently energize the x-ray source to the second voltage at a switching rate that is greater than 550 Hz.

3. The CT system of claim 1 wherein the controller is configured to cause a focal spot of the x-ray source to deflect in a direction orthogonal to a direction of object travel during the imaging session.

4. The CT system of claim 3 wherein the controller is configured to deflect the focal spot to a first location while the x-ray source is energized to the first voltage, and wherein the controller is configured to deflect the focal spot to a second location while the x-ray source is energized to the second voltage.

5. The CT system of claim 1 wherein the controller is configured to synchronize energization of the x-ray source to the first and second voltages with passage of the object through the opening.

6. The CT system of claim 1 wherein the controller is configured to cause a focal spot of the x-ray source to remain at the same focal spot location while the x-ray source is energized to the first voltage and while the x-ray source is energized to the second voltage.

7. The CT system of claim 1 wherein, when the controller determines that the image is adequate to diagnose the suspect pathology, the controller is further configured to diagnose the suspected pathology using the image.

8. The CT system of claim 1 wherein:
when the controller assesses that additional images should be generated, the controller is configured to generate additional images using the first projection and the second projection but with different target densities or different materials, so as provide for diagnosing of the suspect pathology; and
when the controller assesses that additional images should not be generated, the controller is configured to:
identify landmarks or a location of the suspect medical pathology using the first projection and the second projection; and
perform an additional imaging session where CT data is acquired, with a location and range of the CT data being based on the landmarks or location of the suspect medical pathology, as determined by the CT scout imaging data.

9. A method of CT imaging comprising:
passing an object through an opening of a CT system a first time;
projecting a first beam of x-ray energy through the object while a rotatable gantry of the CT system remains stationary and at a circumferential position, the first beam of x-ray energy generated at a first voltage;
acquiring a first projection from the first beam of x-ray energy that projects through the object;
projecting a second beam of x-ray energy through the object while the rotatable gantry of the CT system remains stationary at the circumferential position, the second beam of x-ray energy generated at a second voltage that is different from the first voltage;
acquiring a second projection from the second beam of x-ray energy that projects through the object;
reconstructing an image using the first projection and the second projection;
determining if the image is adequate to diagnose a suspect medical pathology therewith; and
if the image is not adequate to diagnose the suspect medical pathology, then assessing whether to generate additional images, with any additional images that are generated being generated using the first projection and the second projection but with different target densities or different materials, so as provide for diagnosing of the suspect pathology.

10. The method of claim 9 wherein projecting the first beam of x-ray energy comprises projecting the first beam of x-ray energy at approximately 80 kVp, and wherein projecting the second beam of x-ray energy comprises projecting the second beam of x-ray energy at approximately 140 kVp.

11. The method of claim 9 comprising:
evaluating the image for a pathology; and
if a pathology is suspected based on the evaluation, then passing the object through the opening of the CT system a second time while rotating the rotatable gantry and while obtaining dual-energy CT data.

12. The method of claim 11 wherein passing the object through the opening of the CT system a second time while rotating the rotatable gantry and while obtaining dual-energy CT data comprises obtaining one of helical CT data and axial CT data.

13. The method of claim 9 comprising synchronizing passage of the object through the opening of the CT system with a timing signal that switches a generator of the CT system from the first voltage to the second voltage.

14. The method of claim 9 wherein:
projecting the first beam of x-ray energy comprises projecting the first beam of x-ray energy from a first focal spot location; and
projecting the second beam of x-ray energy comprises projecting the second beam of x-ray energy from a second focal spot location that is displaced with respect to the first focal spot location and in a direction substantially orthogonal to a direction through which x-rays project through the object.

15. The method of claim 14 wherein projecting the second beam of x-rays comprises projecting the second beam of x-ray energy from the second focal spot location that is displaced with respect to the first focal spot location in a direction that is orthogonal to a slice direction of the CT system.

16. The method of claim 9 comprising switching between the first beam of x-ray energy and the second beam of x-ray energy at a switching speed that is greater than 550 Hz.

17. The method of claim 9 comprising projecting the first beam of x-ray energy and the second beam of x-ray energy from the same focal spot location in an x-ray tube.

18. The method of claim 9 wherein the steps of determining if the image is adequate to diagnose a suspect medical pathology therewith and assessing whether to generate additional images are performed by a computer associated with the CT system; and
wherein, when the computer assesses that additional images should be generated, additional images are generated using the first projection and the second projection but with different target densities or different materials, so as provide for diagnosing of the suspect pathology; and
wherein, when the computer assesses that additional images should not be generated, landmarks or a location of the suspect medical pathology are identified using the first projection and the second projection.

19. A controller is configured to acquire imaging data at more than one chromatic energy state, wherein the controller is further configured to:
cause an object to pass through an opening of a rotatable gantry while causing the rotatable gantry to remain stationary at a first circumferential position;
cause a voltage potential of an x-ray source to be continuously varied;
cause the x-ray source to project x-ray beams at a plurality of voltage potentials toward the object while the rotatable gantry is at the first circumferential position responsive to the continuous varying of the voltage potential of the x-ray source;
cause acquisition of CT scout data from the x-ray beams by way of an x-ray detector, with flux received by the x-ray detector being equalized based on the continuously varied voltage potential; and
reconstruct an image using the CT scout data, wherein the controller is further configured to:
determine if the reconstructed image is adequate to diagnose a suspect pathology; and
assess whether to generate additional images if the reconstructed image is not adequate to diagnose the suspect pathology, with any additional images that are generated being generated using the first set of data and the second set of data but with different target densities or different materials, so as provide for diagnosing of the suspect pathology.

20. The controller of claim 19 wherein the controller is further configured to cause the object to pass through the opening of the rotatable gantry a second time to acquire dual-energy imaging data, while the rotatable gantry is caused to rotate, if the reconstructed image indicates a presence of a pathology.

21. The controller of claim 19 wherein the controller is configured to deflect the second x-ray beam orthogonally with respect to a location of the first x-ray beam and in a direction that is substantially orthogonal to a direction through which the object is caused to pass through the opening of the rotatable gantry.

22. The controller of claim 19 wherein the controller is configured to cause the first x-ray beam and the second x-ray beam to emit from the same focal spot within the x-ray source.

* * * * *